United States Patent
Watano

(10) Patent No.: US 12,270,742 B2
(45) Date of Patent: Apr. 8, 2025

(54) BIOLOGICAL SPECIMEN SEPARATION INSTRUMENT

(71) Applicant: FUJIFILM Corporation, Tokyo (JP)

(72) Inventor: Hirotaka Watano, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 791 days.

(21) Appl. No.: 17/462,989

(22) Filed: Aug. 31, 2021

(65) Prior Publication Data

US 2021/0396634 A1    Dec. 23, 2021

Related U.S. Application Data

(63) Continuation of application No. PCT/JP2020/012829, filed on Mar. 24, 2020.

(30) Foreign Application Priority Data

Mar. 25, 2019 (JP) .................. 2019-056589

(51) Int. Cl.
*B01L 3/00* (2006.01)
*G01N 1/40* (2006.01)

(52) U.S. Cl.
CPC ............ *G01N 1/4077* (2013.01); *B01L 3/508* (2013.01); *G01N 2001/4088* (2013.01)

(58) Field of Classification Search
CPC ......... G01N 1/4077; G01N 2001/4088; G01N 33/48; B01L 3/508; B01L 2300/042;
(Continued)

(56) References Cited

U.S. PATENT DOCUMENTS

| 4,487,696 A | 12/1984 | Ferrara | |
|---|---|---|---|
| 2003/0175167 A1* | 9/2003 | Takanori | B01L 3/5021 422/534 |

(Continued)

FOREIGN PATENT DOCUMENTS

| JP | 5-52841 A | 3/1993 |
|---|---|---|
| JP | 8-201380 A | 8/1996 |

(Continued)

OTHER PUBLICATIONS

International Preliminary Report on Patentability and Written Opinion of the International Searching Authority (Forms PCT/IB/373 and PCT/ISA/237) for International Application No. PCT/JP2020/012829, dated Sep. 28, 2021, with an English translation.

(Continued)

*Primary Examiner* — Jill A Warden
*Assistant Examiner* — Michael Stanley Gzybowski
(74) *Attorney, Agent, or Firm* — Birch, Stewart, Kolasch & Birch, LLP

(57) ABSTRACT

There is provided a biological specimen separation instrument with which a biological specimen can be stably separated into a predetermined component. The biological specimen separation instrument includes an accommodation instrument (1) for accommodating a collected biological specimen, a filter (128) for filtering a predetermined component in the collected biological specimen, and a holding instrument (100) for accommodating the predetermined component filtered by the filter (128), where the holding instrument (100) is configured to be inserted into the accommodation instrument (1), in which the filter (128) is provided on a tip side of the holding instrument (100) in a direction of insertion into the accommodation instrument (1), a sealing member (130) is provided in an outer circumference on the tip side of the holding instrument (100) in the direction (Continued)

of insertion to allow movement in the accommodation instrument (1), in a state of being liquid-tightly brought into contact with an interior wall of the accommodation instrument (1), and the sealing member (130) has a Shore A hardness of 20 or more and 90 or less and has a residual siloxane concentration of 1 wt % or less.

11 Claims, 17 Drawing Sheets

(58) Field of Classification Search
CPC ..... B01L 2300/0681; B01L 2300/0854; B01L 2400/0478; B01L 3/5023
See application file for complete search history.

(56) References Cited

U.S. PATENT DOCUMENTS

| | | | |
|---|---|---|---|
| 2008/0300397 A1 | 12/2008 | Kenrick et al. | |
| 2011/0008908 A1 | 1/2011 | Biesbrouck | |
| 2014/0042094 A1 | 2/2014 | Montagu et al. | |
| 2015/0153323 A1 | 6/2015 | Huemer | |
| 2015/0231536 A1* | 8/2015 | Nogami | G01N 33/491 210/235 |
| 2016/0355436 A1* | 12/2016 | Chen | C04B 2/045 |
| 2018/0304287 A1* | 10/2018 | Meuler | B05B 7/2408 |

FOREIGN PATENT DOCUMENTS

| | | |
|---|---|---|
| JP | 2003-270239 A | 9/2003 |
| JP | 2007-536 A | 1/2007 |
| JP | 2007-3479 A | 1/2007 |
| JP | 2007-6973 A | 1/2007 |
| JP | 2010-518393 A | 5/2010 |
| JP | 2012-18514 A | 1/2012 |
| JP | 2015-528328 A | 9/2015 |
| JP | 2015-530566 A | 10/2015 |
| WO | WO 2014/064921 A1 | 5/2014 |
| WO | WO-2019025914 A1 * | 2/2019 ....... A61B 5/150022 |

OTHER PUBLICATIONS

International Search Report (Form PCT/ISA/210) for International Application No. PCT/JP2020/012829, dated Jun. 9, 2020, with an English translation.
International Preliminary Report on Patentability and Written Opinion of the International Searching Authority (Forms PCT/IB/373, and PCT/ISA/237) for International Application No. PCT/JP2020/012830, dated Sep. 28, 2021, with an English translation.
International Search Report (Form PCT/ISA/210) for International Application No. PCT/JP2020/012830, dated Jun. 9, 2020, with an English translation.
"Contact Angle;" Wikipedia, 2018, URL: <https://en.wikipedia.org/wiki/Contact_angle>.
"Silicone Rubber," Wikipedia, 2019, URL: <https://en.wikipedia.org/wiki/Silicone_rubber>.
U.S. Office Action for U.S. Appl. No. 17/462,218, dated Jul. 18, 2024.
U.S. Appl. No. 17/462,218, filed Aug. 31, 2021.
Notice of Allowance issued in U.S. Appl. No. 17/462,218 on Feb. 10, 2025.

* cited by examiner

BIOLOGICAL SPECIMEN SEPARATION INSTRUMENT

CROSS-REFERENCE TO RELATED APPLICATIONS

The present application is a Continuation of PCT International Application No. PCT/JP2020/012829 filed on Mar. 24, 2020 claiming priority under 35 U.S.C § 119(a) to Japanese Patent Application No. 2019-056589 filed on Mar. 25, 2019. Each of the above applications is hereby expressly incorporated by reference, in its entirety, into the present application.

BACKGROUND OF THE INVENTION

1. Field of the Invention

The present invention relates to a biological specimen separation instrument and particularly relates to a biological specimen separation instrument in which a collected biological specimen is filtered with a separation membrane.

2. Description of the Related Art

As a method of collecting a biological specimen for collecting and examining a biological specimen, for example, in the case of blood, there are a general blood collection in which a certain qualified person such as a doctor collects blood from a vein using a syringe and a self-blood collection in which an examination subject inserts a blood collection needle into a finger of the hand of the examination subject to collect blood.

The blood collected by the general blood collection is transported to a medical institution or an examination institution in a state of being sealed in a collection container, and the examination is carried out there. In a case where the blood sample is transported without being separated into blood cells and plasma or serum, the examination is carried out after the blood sample is separated into blood cells and plasma or serum by a centrifuge at the medical institution or the examination institution. In the self-blood collection carried out by an examination subject, the blood sample after the blood collection is separated into blood cells and plasma or serum by a separation membrane and, in the state of being separated, transported to an examination site where the examination is carried out.

In a case where self-blood collection is carried out, the blood separation is carried out using a separation instrument. For example, JP2007-6973A discloses a blood collection and separation device that collects blood and separates the collected blood into blood cells and plasma or serum using a filter member. In the blood collection and separation device, a gasket is used to allow movement in the lengthwise direction in a state where a first container and a second container are air-tightly brought into contact with each other.

In addition, JP2003-270239A discloses a biological specimen separation instrument that includes a biological specimen collection unit for accommodating a collected biological specimen, a filtering unit for causing a predetermined component in the collected biological specimen to pass, and a separated component accommodation unit for accommodating the predetermined component that has passed through the filtering unit. In a case where a tube body is fitted into the blood collection container, the tube body is lowered in a state where a cover made of silicone rubber, provided on the outer circumference of the tube body, is closely attached to the inner surface of the blood collection container.

SUMMARY OF THE INVENTION

For separating blood using a filter, it is necessary to maintain the hydrophilicity of the filter. However, in a case where the gasket is made of silicone rubber, there has been a case where the filter is hydrophobized due to the influence of the siloxane generated from the silicone rubber. In a case where the filter was hydrophobized, blood cells did not enter the central part of the filter, and the blood cells intruded between the filter and the holding part that holds the filter, whereby the blood cells were destroyed by the filter, that is, hemolysis occurred.

As the material of the gasket, JP2007-6973A uses a material having rubber elasticity, and JP2003-270239A uses a cover made of silicone rubber. As described above, in JP2007-6973A and JP2003-270239A, the siloxane generated from the gasket was not taken into account, and a material that suppresses the generation of siloxane was not taken into account.

The present invention has been made in consideration of such circumstances, and an object of the present invention is to provide a biological specimen separation instrument with which a biological specimen can be stably separated into a predetermined component by preventing the hydrophobization of a filter for separating the biological specimen.

For achieving the object of the present invention, a biological specimen separation instrument according to an aspect of the present invention includes a first container for accommodating a collected biological specimen, a filter for filtering a predetermined component in the collected biological specimen, and a second container for accommodating the predetermined component filtered by the filter, the second container being configured to be inserted into the first container, where the filter is provided on a tip side of the second container in a direction of insertion into the first container, a sealing member is provided in an outer circumference on the tip side of the second container in the direction of insertion to allow movement in the first container, in a state of being liquid-tightly brought into contact with an interior wall of the first container, and the sealing member has a Shore A hardness of 20 or more and 90 or less and has a residual siloxane concentration of 1 wt % or less.

According to the biological specimen separation instrument according to the aspect of the present invention, the residual siloxane concentration of the sealing member that is provided on the outer circumference of the second container and liquid-tightly comes into contact with the first container is set to 1 wt % or less, and thus the generation of siloxane can be suppressed, whereby the filter can be prevented from being hydrophobized. Further, in a case where the Shore A hardness of the sealing member is set to 20 or more and 90 or less, the smoothness between the first container and the second container can be ensured.

DESCRIPTION OF THE PREFERRED EMBODIMENTS

Hereinafter, a biological specimen separation instrument according to an embodiment of the present invention will be described with reference to the attached drawings. In the present invention, the numerical value range indicated by using "to" means a range including the numerical values before and after "to" as the lower limit value and the upper limit value, respectively.

[Biological Specimen Separation Instrument]

Figure 1:
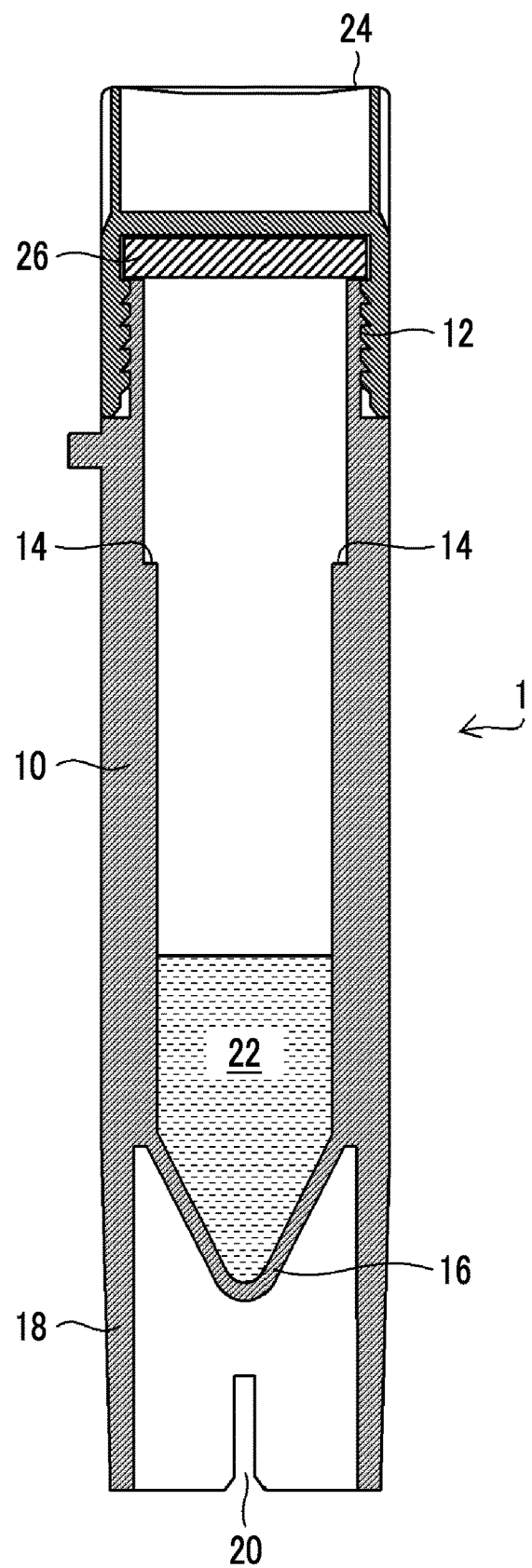
FIG. 1 is a cross-sectional view illustrating an example of a configuration of an accommodation instrument.
Figure 2:
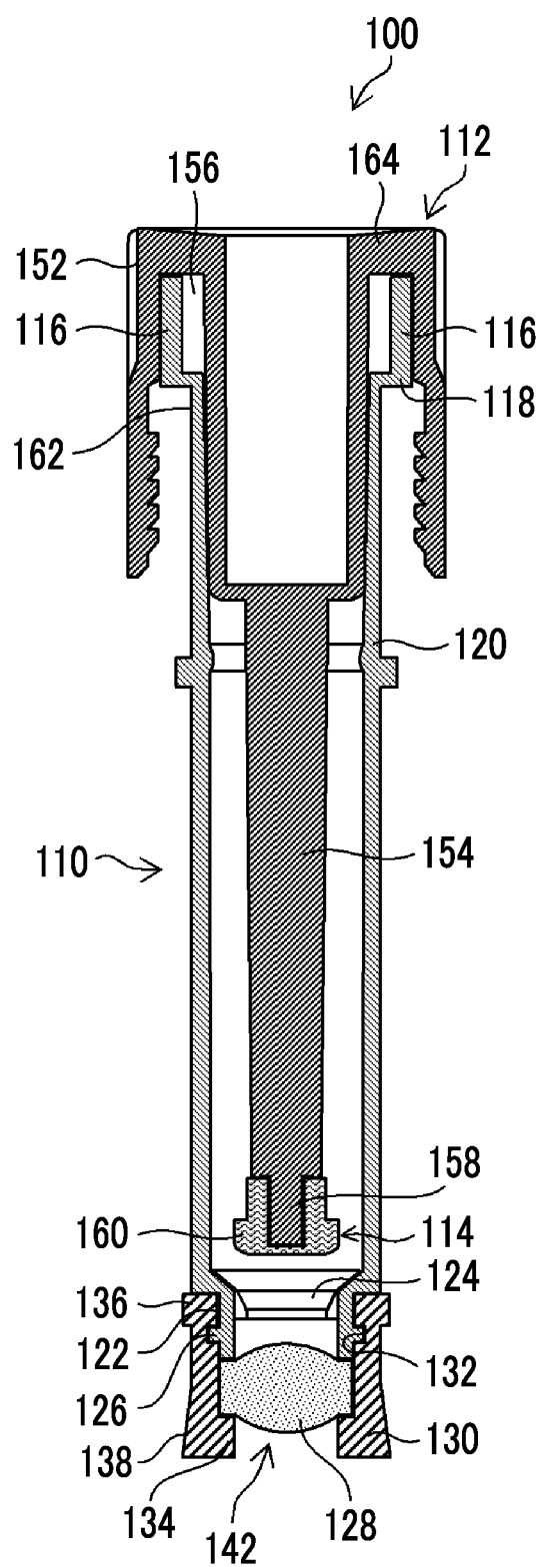
FIG. 2 is a cross-sectional view illustrating an example of a configuration of a holding instrument having a filter.
Figure 3:
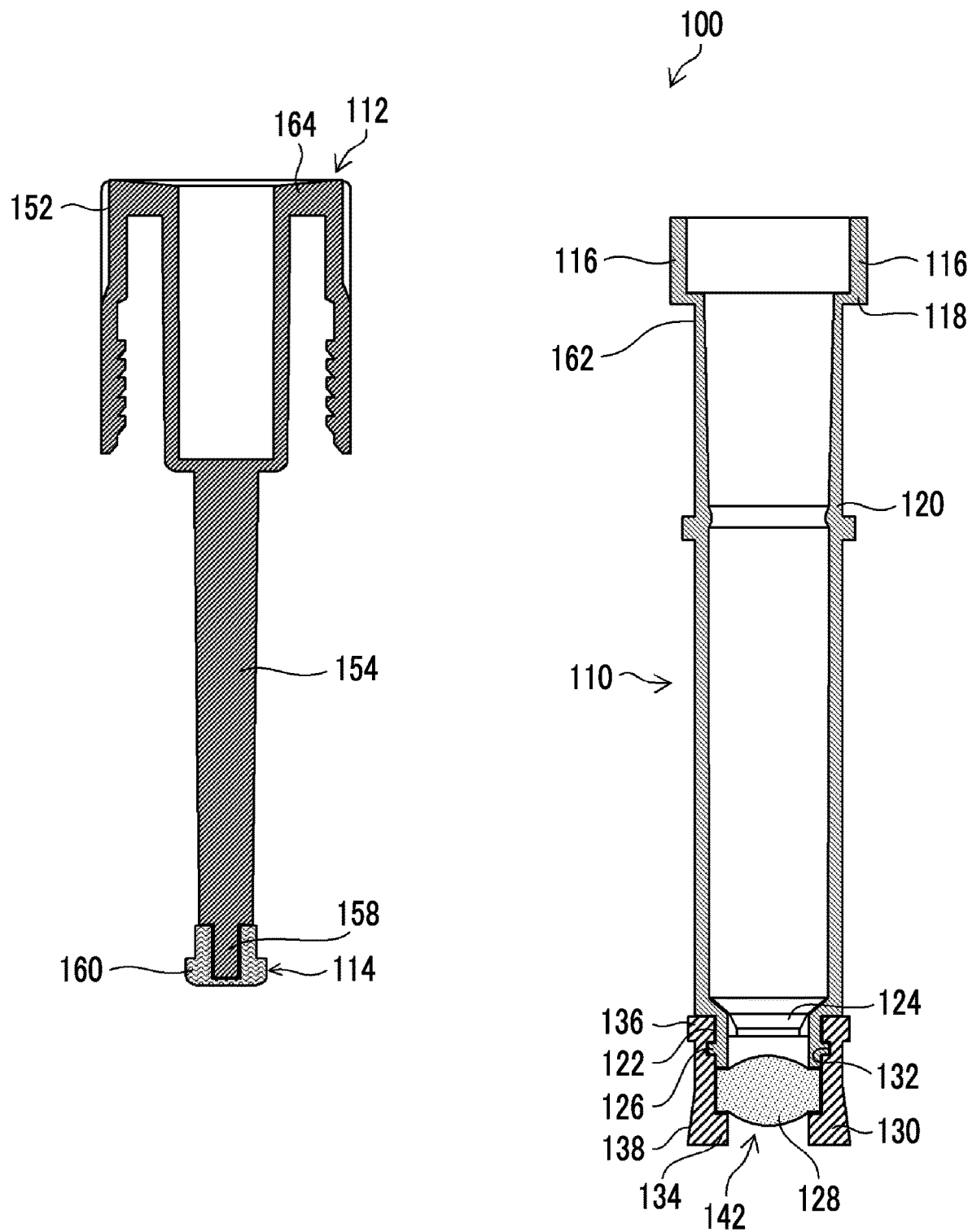
FIG. 3 is a disassembled cross-sectional view of the holding instrument disassembled into a cylinder and a cap.
Figure 4:
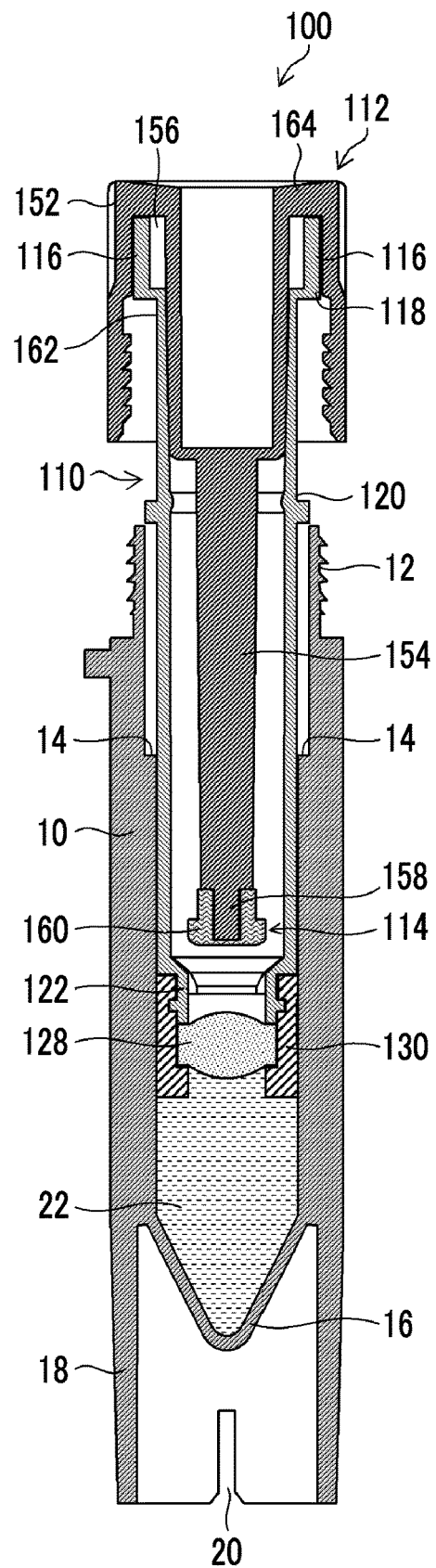
FIG. 4 is a view for explaining a state where the holding instrument is inserted into the accommodation instrument.
Figure 5:
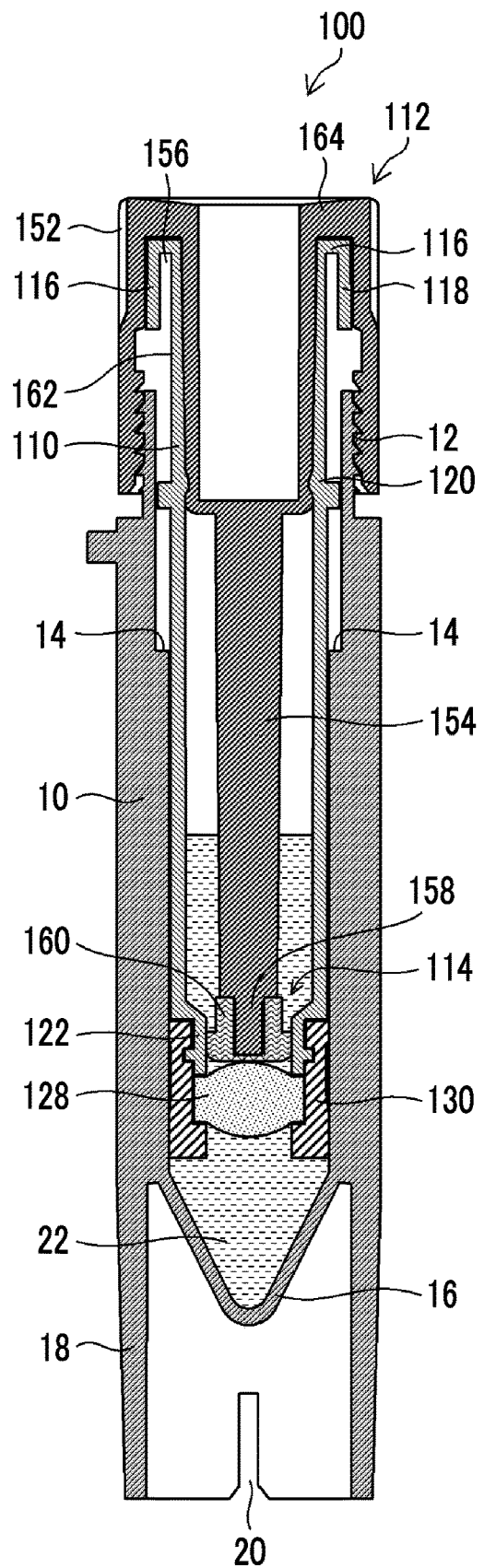
FIG. 5 is a view for explaining a state after separating a biological specimen using a separation instrument.
Figure 6:
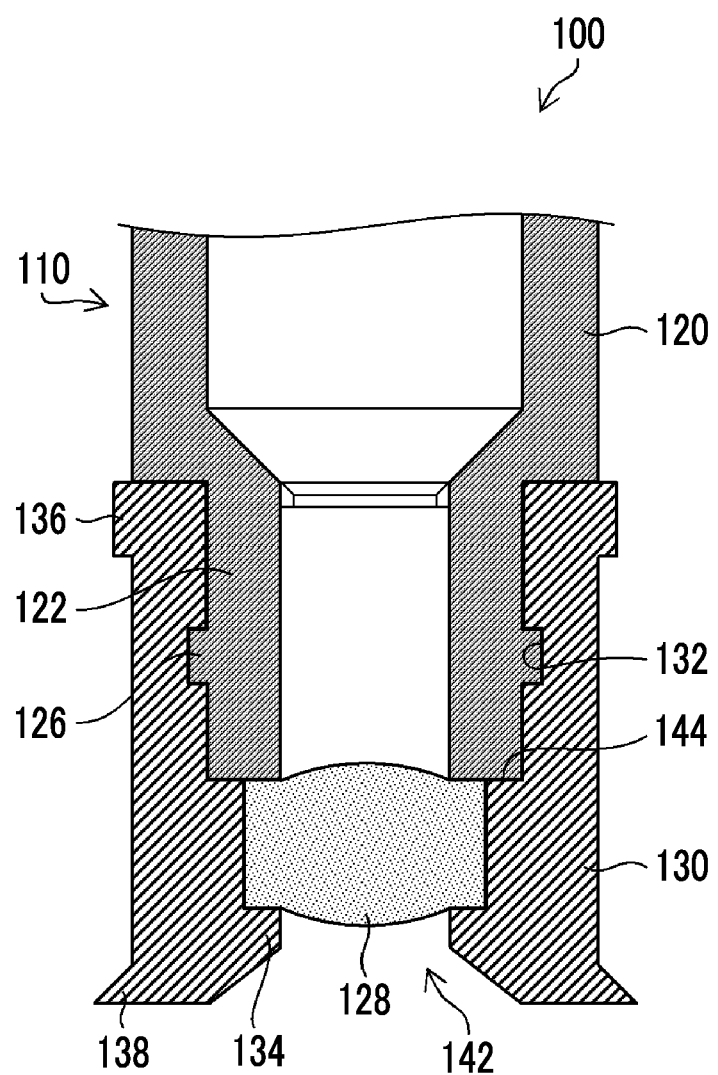
FIG. 6 is an enlarged view of a tip part of the holding instrument illustrated in FIG. 2.

The biological specimen separation instrument will be described with reference to FIG. 1 to FIG. 6. FIG. 1 is a cross-sectional view illustrating an example of a configuration of an accommodation instrument (a first container), and FIG. 2 is a cross-sectional view illustrating an example of a configuration of a holding instrument (a second container) having a filter. FIG. 3 is a disassembled cross-sectional view of the holding instrument illustrated in FIG. 2, which is disassembled into a cylinder and a cap. FIG. 4 is a view for explaining a state where the holding instrument is inserted into the accommodation instrument, and FIG. 5 is a view for explaining a state where a biological specimen is separated by a separation instrument provided in the holding instrument. FIG. 6 is an enlarged view of a tip part of the holding instrument. In the following description, the description will be made using blood as an example of the biological specimen; however, the biological specimen of the present embodiment is not limited to blood and other biological specimens can also be used.

<<Accommodation Instrument (First Container)>>

As illustrated in FIG. 1, an accommodation instrument 1 has a cylindrical blood collection container 10 made of a transparent material. On the upper end side of the blood collection container 10, a screw part 12 is formed on the outer surface, and a locking part 14 is provided to protrude on the inner surface. In addition, a conical bottom part 16 protruding toward the lower end side is formed at the lower end part of the blood collection container 10. A cylindrical leg part 18 is formed around the bottom part 16. Here, the "upper" and the "lower" respectively mean "upper" and "lower" in a state where the leg part 18 is installed on the placement surface.

The leg part 18 has the same outer diameter as the sample cup (not illustrated in the drawing) that is used in the analysis and examination of the blood, and a slit groove 20 is preferably formed at a position where the leg parts face each other at the lower end thereof, in the vertical direction. Further, as illustrated in FIG. 1, the blood collection container 10 preferably accommodates a diluent 22 of a required amount, for example, 500 mm$^3$.

As illustrated in FIG. 1, in the accommodation instrument 1 before use, it is preferable that an upper end opening of the blood collection container 10 is sealed by a cap 24 through a packing 26. Further, in a case of collecting blood, it is preferable that the upper end opening is sealed by the cap 24 and the packing 26 after the cap 24 is removed and blood is collected.

For blood collection in the blood collection container 10, blood can be collected directly. In addition, a blood sample can be collected by absorbing blood into an absorbent material and putting the absorbent material into the blood collection container 10.

<<Holding Instrument (Second Container)>>

There is a possibility that a long time elapses until the carrying out of the analysis of the collected blood sample which is in a state of being diluted in the accommodation instrument 1. During this time, there is a possibility that in a case where hemolysis of red blood cells occurs, substances and enzymes that are present in the blood cells are eluted into plasma or serum, which affects the examination results, or the optical absorption of the eluted hemoglobin affects a case of a measurement in which an amount of an analysis target component is measured with optical information such as the optical absorption of the analysis target component. Accordingly, it is preferable to prevent hemolysis. For this reason, a predetermined component (a plasma component in the present embodiment) is separated from the diluted blood sample with a filter, and the separated plasma component is accommodated in the holding instrument. The filter is preferably provided in the holding instrument, and the plasma component that has passed through the filter is directly accommodated in the holding instrument. The filter can be used so that, for example, pressure is applied to a diluted blood sample to capture a blood cell component with the filter and the plasma component is allowed to pass to separate blood cells, whereby the plasma component is recovered. In this case, it is preferable to use an anticoagulant. Further, for ensuring the accuracy of the measurement, it is preferable that the plasma that has passed through the filter does not flow back to the blood cell side. Therefore, specifically, the backflow prevention unit disclosed in JP2003-270239A can be provided in the holding instrument.

FIG. 2 is a cross-sectional view illustrating an example of a configuration of a holding instrument 100 having a filter 128. The holding instrument 100 illustrated in FIG. 2 is composed by combining a cylinder 110 and a cap 112. The cylinder 110 is configured to be inserted into the blood collection container 10 of the accommodation instrument 1. The cap 112 is screwable to the accommodation instrument 1, and a sealing member 114 that prevents the plasma in the cylinder 110 from flowing back into the blood collection container 10 is provided at the lower end of the cap 112.

The cylinder 110 is made of a transparent material and has a cylindrical shape. An expanded diameter part 116 is formed at an upper end part 162 of the cylinder 110. The expanded diameter part 116 is connected to a body part 120 through a thin-wall portion 118. As illustrated in FIG. 6, a reduced diameter part 122 is formed at the lower end part of the cylinder 110. A locking protrusion part 124 is formed on the inner surface of the reduced diameter part 122. Further, an outer flange part 126 is formed on the outside of the reduced diameter part 122. The filter 128 is provided on the lower end side of the reduced diameter part 122, that is, on the tip side in the direction of insertion into the accommodation instrument 1. The filter 128 is configured to allow the passage of the plasma in the blood and block the passage of the blood cells. A sealing member 130 is mounted on the outside of the reduced diameter part 122 and the outside of the filter 128. With the sealing member 130, the liquid tightness between the blood collection container 10 and the cylinder 110 in a case where the cylinder 110 is fitted into the blood collection container 10 can be held. Further, the smoothness between the blood collection container 10 and the cylinder 110 can be ensured. The sealing member 130 has a groove 132 on the inner surface thereof, and thus it is possible to prevent the sealing member 130 from falling from the reduced diameter part 122 since the outer flange part 126 fits to the groove 132. Further, a stepped part 144 is provided in the inner circumference of the sealing member 130, and the tip of the reduced diameter part 122 is in contact with the stepped part 144. A first protrusion part 134 protruding inward is provided on the lower end side of the sealing member 130. The filter 128 is held by being sandwiched, in the vertical direction, between the reduced diameter part 122 of the cylinder 110 and the first protrusion part 134 of the sealing member 130. The inner opening formed by the first protrusion part 134 serves as an inflow port 142 into which the blood flows from the blood collection container 10. In the sealing member 130, a second protrusion part 136 is provided in the outer circumference of the upper end part, and a third protrusion part 138 is provided in the outer circumference of the lower end part. The outer diameters of the second protrusion part 136 and the third protrusion part 138 of the sealing member 130 are larger than the outer diameter of the body part 120.

As the filter 128, it is preferable to use a hydrophilic filter since it is necessary to filter blood. Specifically, it is preferable to use a depth filter. Further, in FIG. 2, FIG. 3, and FIG. 6, although the description is made using the configuration in which one filter is used described, a configuration having two or more depth filters may be used.

The cap 112 is composed of a substantially cylindrical grip part 152 and a mandrel part 154 that is concentric with the grip part 152 and extends downward. A cylindrical space 156 to which the expanded diameter part 116 of the cylinder 110 is capable of fitting is formed in the inner upper end part of the grip part 152, and the lower portion thereof is screwed to be screwable to a screw. A lower end part 158 of the mandrel part 154 is formed in a pin shape, and the sealing member 114 is provided attachably and detachably in the lower end part 158. The sealing member 114 is made of silicone rubber. The lower end part of the sealing member 114 has a substantially columnar shape formed in an outer flange shape, and a stepped part 160 is formed around the outer circumference. The grip part 152 has an apex part 164, and the inner surface of the apex part 164 comes into contact with the expanded diameter part 116. The cylinder 110 and the cap 112 may not be combined until they are used, and may be used by being combined by a user in a case of being used. Alternatively, the cylinder 110 and the cap 112 may be combined from the beginning.

Next, a blood separation method after collecting blood will be described with reference to FIG. 4 and FIG. 5. First, the cap 24 is removed, and the cylinder 110 to which the cap 112 is attached is fitted into the blood collection container 10, where the blood collection container 10 have accommodated a diluted blood sample.

Next, as illustrated in FIG. 4, the grip part 152 is screwed to the screw part 12. First, the grip part 152 and the cylinder 110 rotate. When the locking part 14 of the blood collection container 10 is locked to a stopper part (not illustrated in the drawing) formed on the outer circumference surface of the cylinder 110, the rotation of the cylinder 110 is restricted, and the thin-wall portion 118 is ruptured by twisting. As a result, the cylinder 110 is separated into the body part 120 and the expanded diameter part 116. In a case where the grip part 152 is further rotated, the upper end part 162 of the body part 120 enters the space 156 inside the expanded diameter part 116. Since the cylinder 110 is pressed downward by the inner surface of the apex part 164 of the grip part 152, the cylinder 110 is further lowered.

As the cylinder 110 is lowered, the filter 128 held by the cylinder 110 moves to the bottom part 16 of the blood collection container 10. At that time, plasma moves to the side of the cylinder 110 through the filter 128, and blood cells cannot pass through the filter 128 and thus remain on the side of the blood collection container 10.

Since the outer diameters of the second protrusion part 136 and the third protrusion part 138 of the sealing member 130 are larger than the outer diameter of the body part 120 of the cylinder 110, the cylinder 110 is movable in a state of liquid-tightly coming into contact with the interior wall of the blood collection container 10. As a result, in the process of fitting the cylinder 110 into the blood collection container 10, there is no possibility that the blood or the diluent 22 in the blood collection container 10 leaks to the outside through the gap between the blood collection container 10 and the cylinder 110.

In a case where the grip part 152 is screwed to the screw part 12 up to the lowermost part, the sealing member 114 fits to the reduced diameter part 122. The flow channel between the blood collection container 10 and the cylinder 110 is sealed by the sealing member 114. The sealing member 114 prevents the mixing of the plasma and the blood cells due to backflow. As a result, the state of separation into blood cells and plasma or serum is reliably held.

[Configuration of Sealing Member]

Next, the configuration of the sealing member 130 will be described. In the present embodiment, the generation of siloxane from the sealing member 130 is suppressed, whereby the hydrophobization of the filter 128 is prevented. As the material of the sealing member 130, a material having a residual siloxane concentration of 1 wt % or less after production is used. Preferably, a material having a residual siloxane concentration of 0.01 wt % or less is used. In a case where the residual siloxane concentration is set to the above numerical value or less, the generation of siloxane can be suppressed, whereby the hydrophobization of the filter 128 can be prevented. The siloxane concentration can be measured by immersing 30 mg of a sample (a sealing member) in a mixed solution of 1 mL of hexane and 0.5 mL of toluene for 12 hours and quantifying the sample by gas chromatography-mass spectrometry (GC-MS). In order to prevent the hydrophobization of the filter 128, it is also effective to make it difficult to generate at least any one of a low molecular weight component, a volatile component, or an elution component.

Further, as described above, since the cylinder 110 is lowered in a state where the sealing member 130 is closely attached to the inner surface of the blood collection container 10, the sealing member 130 preferably has smoothness. In order to impart the smoothness to the sealing member 130, the Shore A hardness of the sealing member 130 is set to be, for softness, 20 or more and 90 or less. In a case where the Shore A hardness is set within the above range, both the liquid tightness and the smoothness can be achieved between the blood collection container 10 and the sealing member 130. Regarding the Shore A hardness, a numerical value measured according to JIS K 6253 can be used.

As the material of the sealing member 130, any one of fluororubber, isoprene rubber, butyl rubber, chlorinated butyl rubber, and a thermoplastic elastomer can be used. As the thermoplastic elastomer, any one of a polystyrene-based thermoplastic elastomer, a polyolefin-based thermoplastic elastomer, a vinyl chloride-based thermoplastic elastomer, a polyurethane-based thermoplastic elastomer, a polyester-based thermoplastic elastomer, a polyamide-based thermoplastic elastomer, and a polybutadiene-based thermoplastic elastomer can be used. In a case where the sealing member 130 is composed of the above-described material, it is possible to suppress or prevent the generation of siloxane from the sealing member 130.

The filter 128 is held by being pressed by the tip of the reduced diameter part 122 of the cylinder 110 and the first protrusion part 134 in the vertical direction and from the periphery by the sealing member 130. That is, the filter 128 is directly held by the sealing member 130. Due to being pressed in the vertical direction by the tip of the reduced diameter part 122 and the first protrusion part 134 of the sealing member 130, the thickness of the central part of the filter 128 is thicker than that of the end part. That is, the end part of the filter 128 is held by being compressed and thinned. This can make it difficult for blood to pass through the end part of the filter 128 in a case of being filtered. As a result, blood can be filtered at the central part of the filter 128. In addition, since the intrusion in the end part direction can be suppressed, hemolysis can be prevented.

Figure 7:
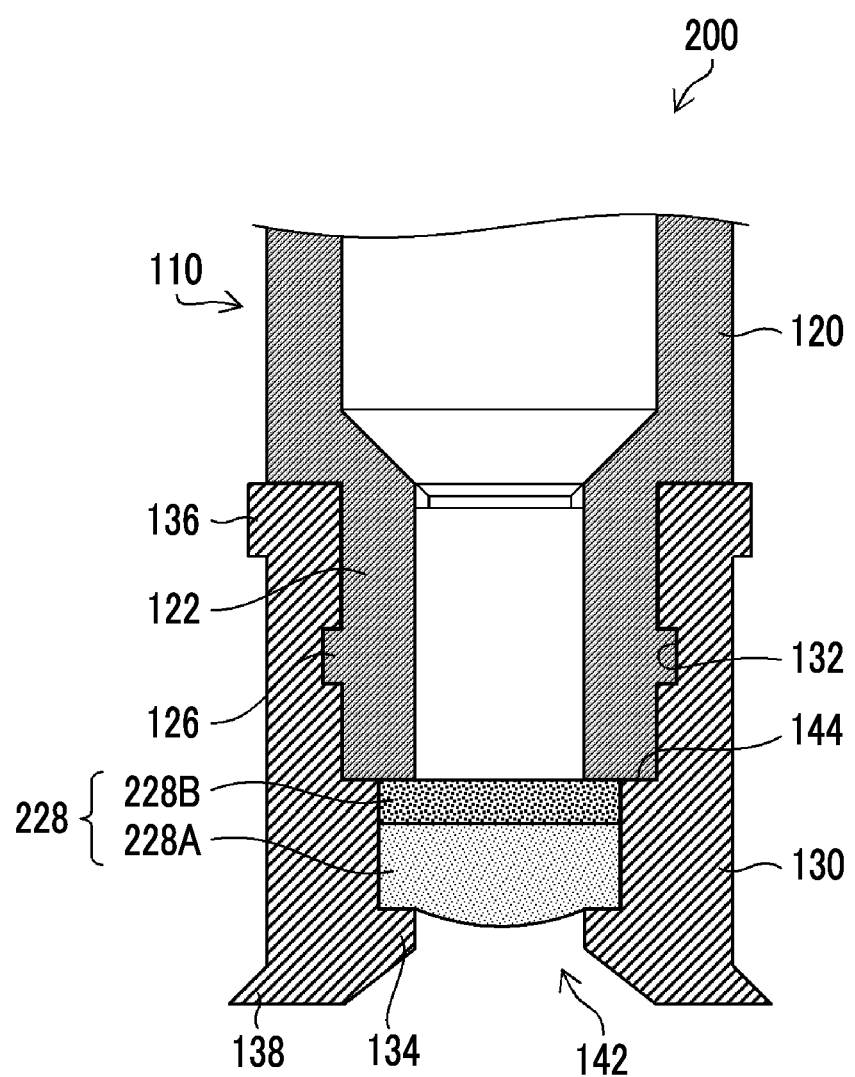
FIG. 7 is an enlarged view of another embodiment of the tip part of the holding instrument.
Figure 8:
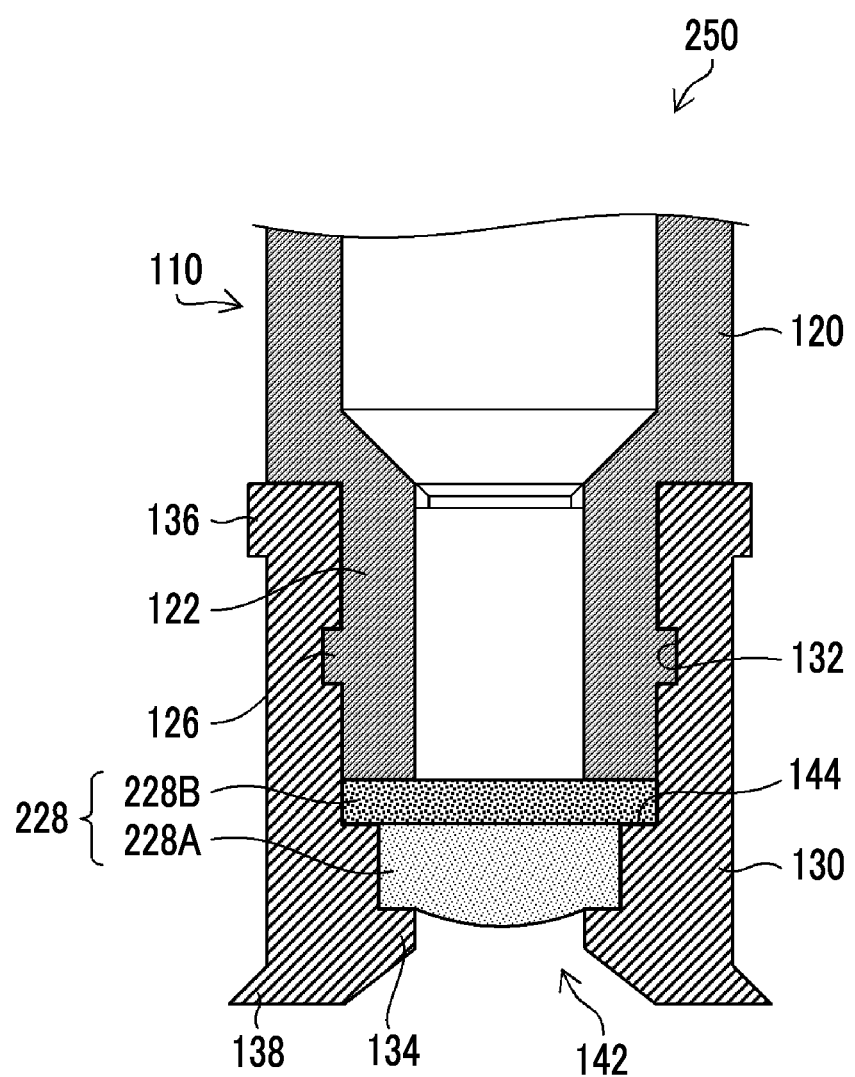
FIG. 8 is an enlarged view of still another embodiment of the tip part of the holding instrument.
Figure 9:
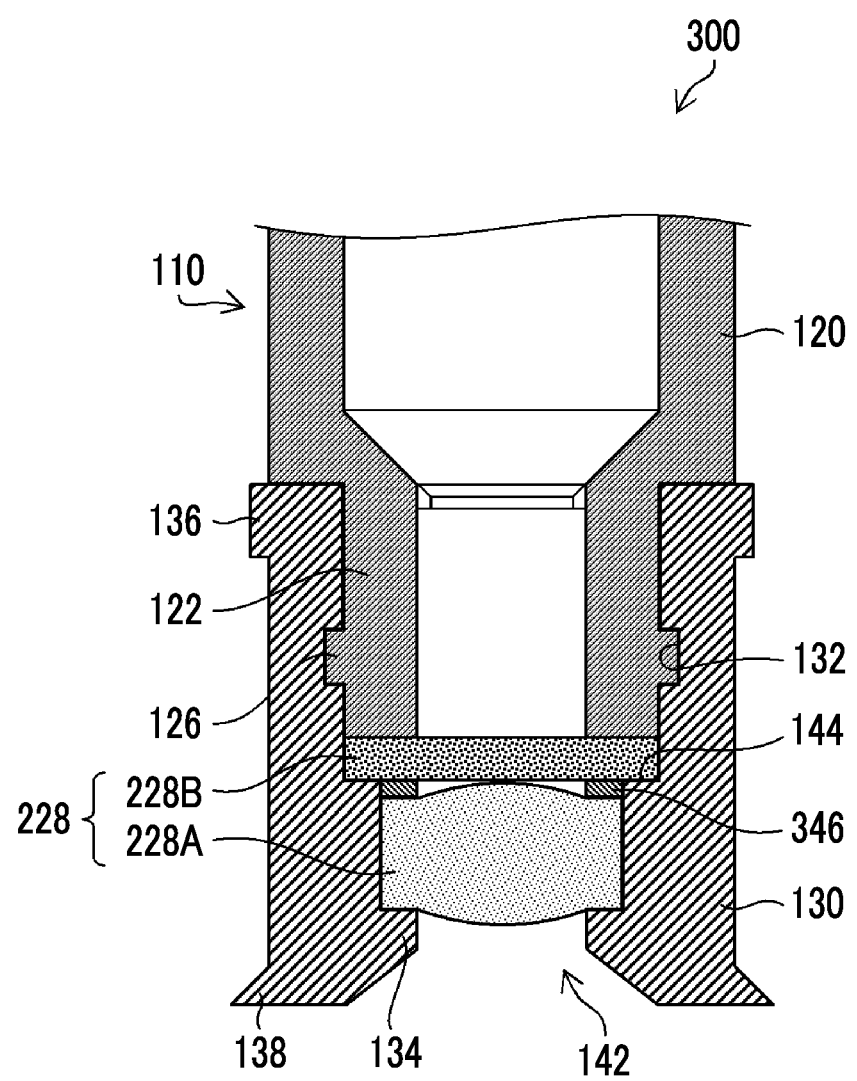
FIG. 9 is an enlarged view of still another embodiment of the tip part of the holding instrument.

FIG. 7 to FIG. 9 are enlarged views illustrating other configurations of the filter and the sealing member provided at the tip of the holding instrument. FIG. 6 is an enlarged view of the configuration described with reference to FIG. 2 to FIG. 5.

In the holding instrument 200 illustrated in FIG. 7, a filter 228 is composed of two filters and has a first filter 228A which is a depth filter and a second filter 228B which is a membrane filter, in order from the inflow port 142 side. Since the filter 228 has two filters which are the depth filter and the membrane filter, a blood cell component can be reliably captured by the membrane filter even in a case where the blood cell component passes through the depth filter. In FIG. 7 as well, the first filter 228A is composed of one depth filter; however, it may be composed of two or more depth filters.

In the holding instrument illustrated in FIG. 7, the first filter 228A and the second filter 228B are arranged to overlap each other, where the filter 228 is held due to being pressed by the first protrusion part 134 of the sealing member 130 and the tip of the reduced diameter part 122.

FIG. 8 is an enlarged view illustrating still another embodiment of the tip part of the holding instrument. In a holding instrument 250 illustrated in FIG. 8, the first filter 228A and the second filter 228B are arranged to overlap each other, where the filter 228 is held due to being pressed by the first protrusion part 134 of the sealing member 130 and the tip of the reduced diameter part 122. In the holding instrument 250 illustrated in FIG. 8, the second filter 228B has a larger area than the first filter 228A. In addition, a protrusion portion of the second filter 228B, which does not overlap with the first filter 228A, is pressed by the reduced diameter part 122 and the stepped part 144 of the sealing member 130, whereby the second filter 228B is held. With such a configuration, the end part of the second filter 228B can be reliably compressed and held. As a result, it is possible to prevent the intrusion of the blood, which prevents hemolysis.

FIG. 9 is an enlarged view of still another embodiment of the tip part of the holding instrument. The holding instrument 300 illustrated in FIG. 9 differs from the holding instrument 250 illustrated in FIG. 8 in that a spacer 346 is provided between the first filter 228A and the second filter 228B. As illustrated in FIG. 9, since the spacer 346 is provided, first, the second filter 228B is pressed and held by the reduced diameter part 122 of the cylinder 110 and the stepped part 144 of the sealing member 130 in the same manner as in FIG. 8. In addition, the first filter 228A is pressed by the reduced diameter part 122 and the first protrusion part 134 and is held through the second filter 228B and the spacer 346. Further, the second filter 228B is held by the reduced diameter part 122 and the stepped part 144, and, in addition, is pressed by the reduced diameter part 122 and the first protrusion part 134 to be held through the first filter 228A and the spacer 346. Since the spacer 346 is provided between the first filter 228A and the second filter 228B, the first filter 228A can be pressed by the first protrusion part 134 and the spacer 346. Further, the second filter 228B can be pressed by the reduced diameter part 122 and the spacer 346. As a result, the first filter 228A and the second filter 228B can be reliably held.

Since the end part of the filter is reliably held by being compressed, it is possible to prevent the blood collected in the blood collection container 10 from not passing through the filter and from intruding between the filter and the sealing member. As a result, blood separation can be reliably carried out, and hemolysis can be prevented.

FIG. 10 to FIG. 13 are enlarged views of still another embodiment of the tip part of the holding instrument. In the tip part of the holding instrument illustrated in FIG. 10 to FIG. 13, the filter is held by being pressed by the reduced diameter part of the cylinder and the first protrusion part of the sealing member in the vertical direction and is held by the sealing member through the holder from the side. Since the filter is held through the holder, it is possible to reduce the area in which the filter comes into direct contact with the sealing member. As a result, even in a case where siloxane is generated from the sealing member, the filter can be prevented from being hydrophobized. However, in a case where the sealing member is directly held by the seal member without the holder being provided, the filter can be compressed by the elastic force of the sealing member, and thus it is possible to prevent the intrusion of the blood.

Figure 10:
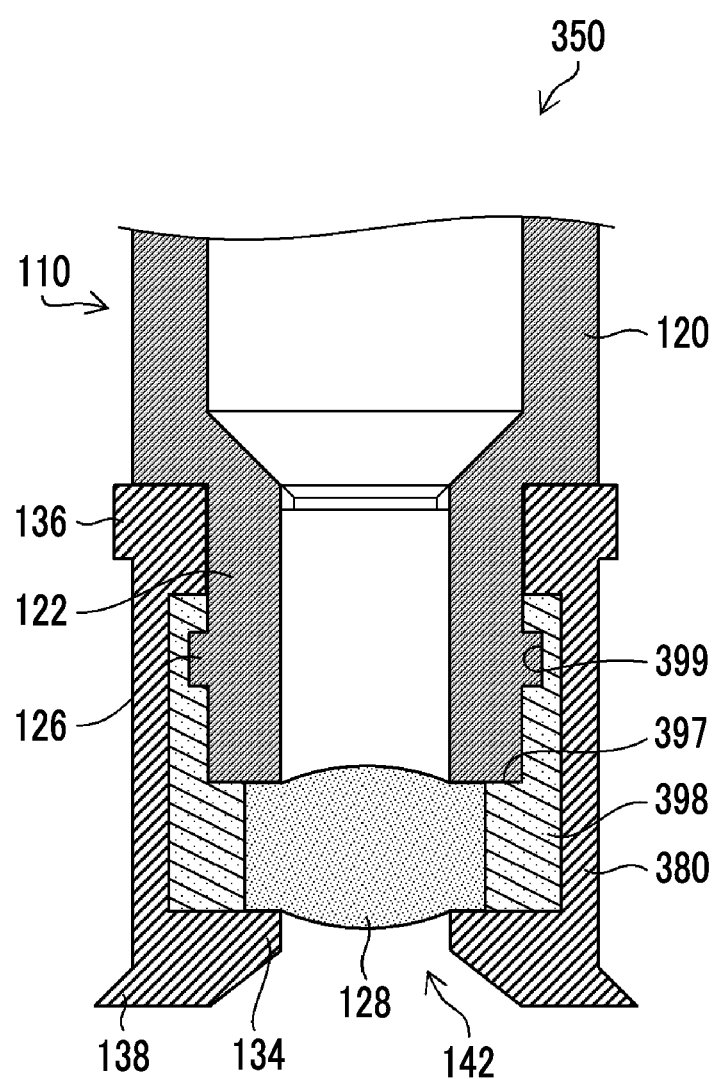
FIG. 10 is an enlarged view of still another embodiment of the tip part of the holding instrument.

In the holding instrument 350 illustrated in FIG. 10, the groove 399 provided in the holder 398 is fitted to the outer flange part 126 provided on the outside of the reduced diameter part 122 to fix the position of the holder 398. Further, the sealing member 380 is fitted from the side to hold, whereby the holder 398 is held. The filter 128 is held in the vertical direction by being pressed by the reduced diameter part 122 of the cylinder 110 and the first protrusion part 134 of the sealing member 380. In addition, the holder 398 has a stepped part 397, and the reduced diameter part 122 of the cylinder 110 is in contact with the stepped part 397.

Figure 11:
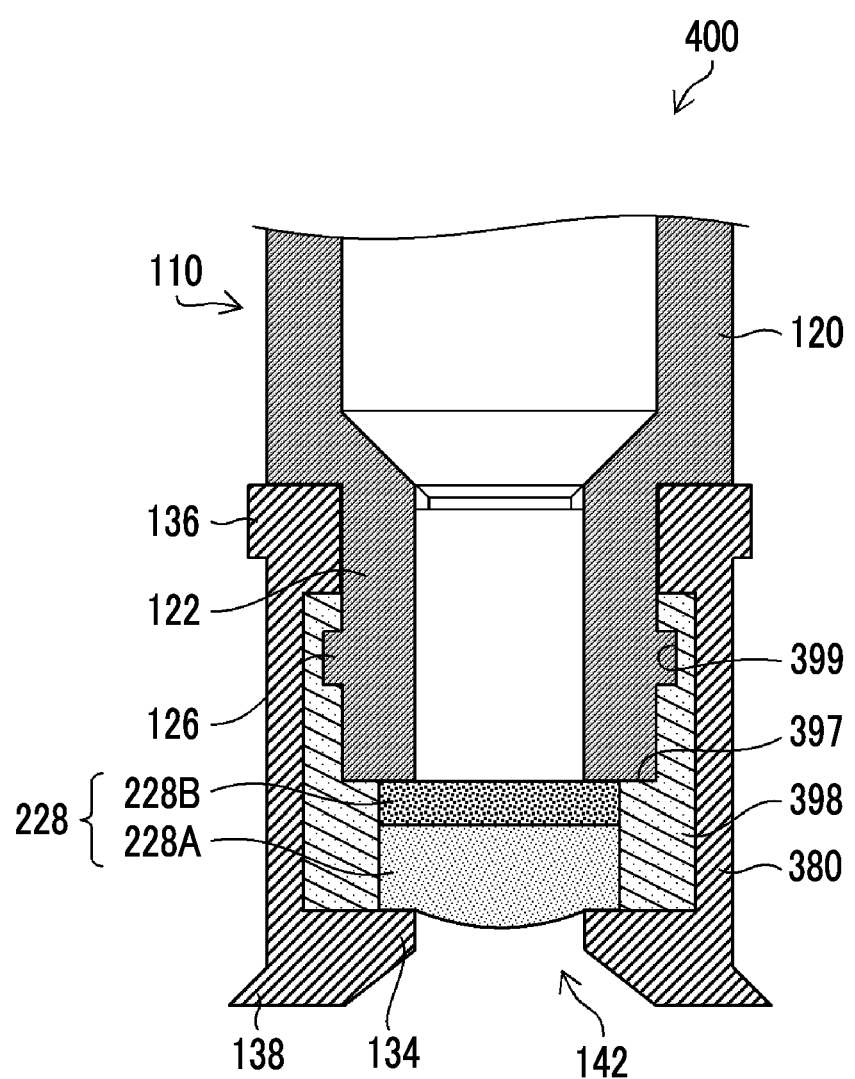
FIG. 11 is an enlarged view of still another embodiment of the tip part of the holding instrument.

The holding instrument 400 illustrated in FIG. 11 has a first filter 228A which is a depth filter and a second filter 228B which is a membrane filter, in order from the inflow port 142 side. The first filter 228A and the second filter 228B are overlapped and are held by being pressed by the tip of the reduced diameter part 122 and the first protrusion part 134 of the sealing member 130. Further, they are held by the holder 398 from the side.

Figure 12:
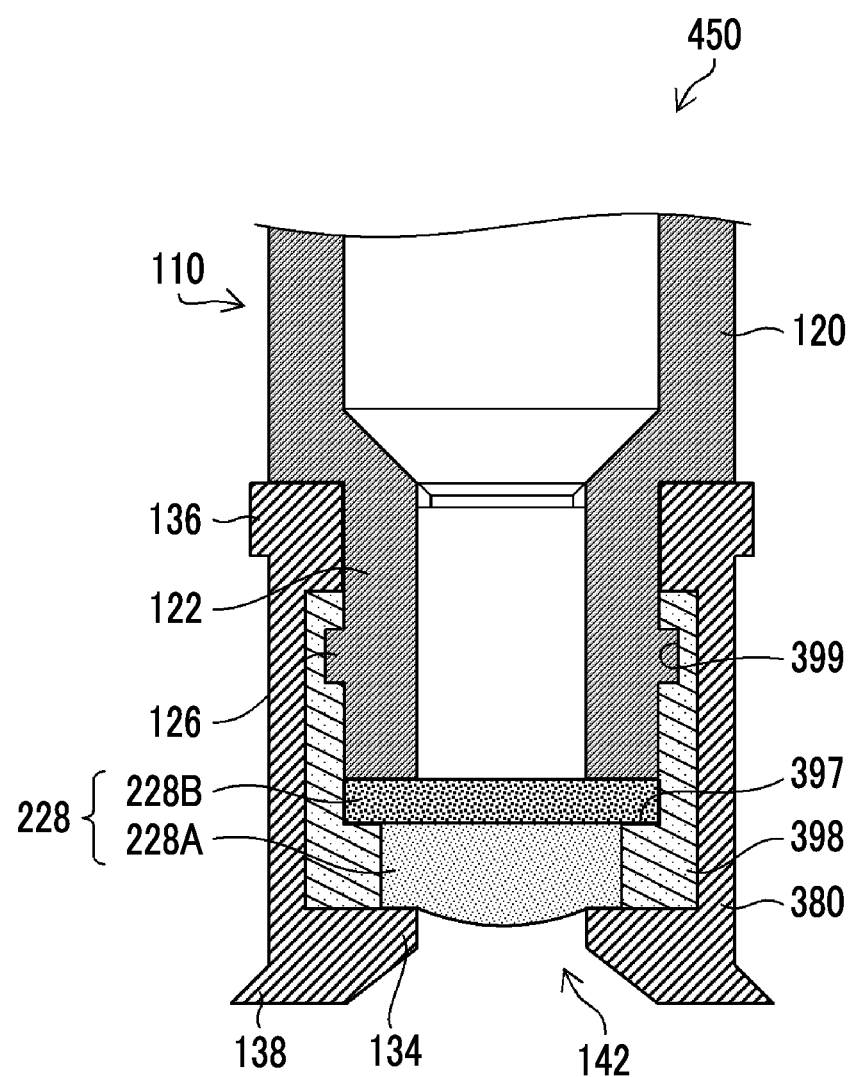
FIG. 12 is an enlarged view of still another embodiment of the tip part of the holding instrument.

FIG. 12 is an enlarged view illustrating still another embodiment of the tip part of the holding instrument. In a holding instrument 450 illustrated in FIG. 12, the first filter 228A and the second filter 228B are arranged to overlap each other, where the filter 228 is held due to being pressed by the first protrusion part 134 of the sealing member 130 and the tip of the reduced diameter part 122. In the holding instrument 450 illustrated in FIG. 12, the second filter 228B has a larger area than the first filter 228A. In addition, a protrusion portion of the second filter 228B, which does not overlap with the first filter 228A, is pressed by the reduced diameter part 122 and the stepped part 397 of the holder 398, whereby the second filter 228B is held. With such a configuration, the end part of the second filter 228B can be reliably compressed and held. As a result, it is possible to prevent the intrusion of the blood, which prevents hemolysis.

Figure 13:
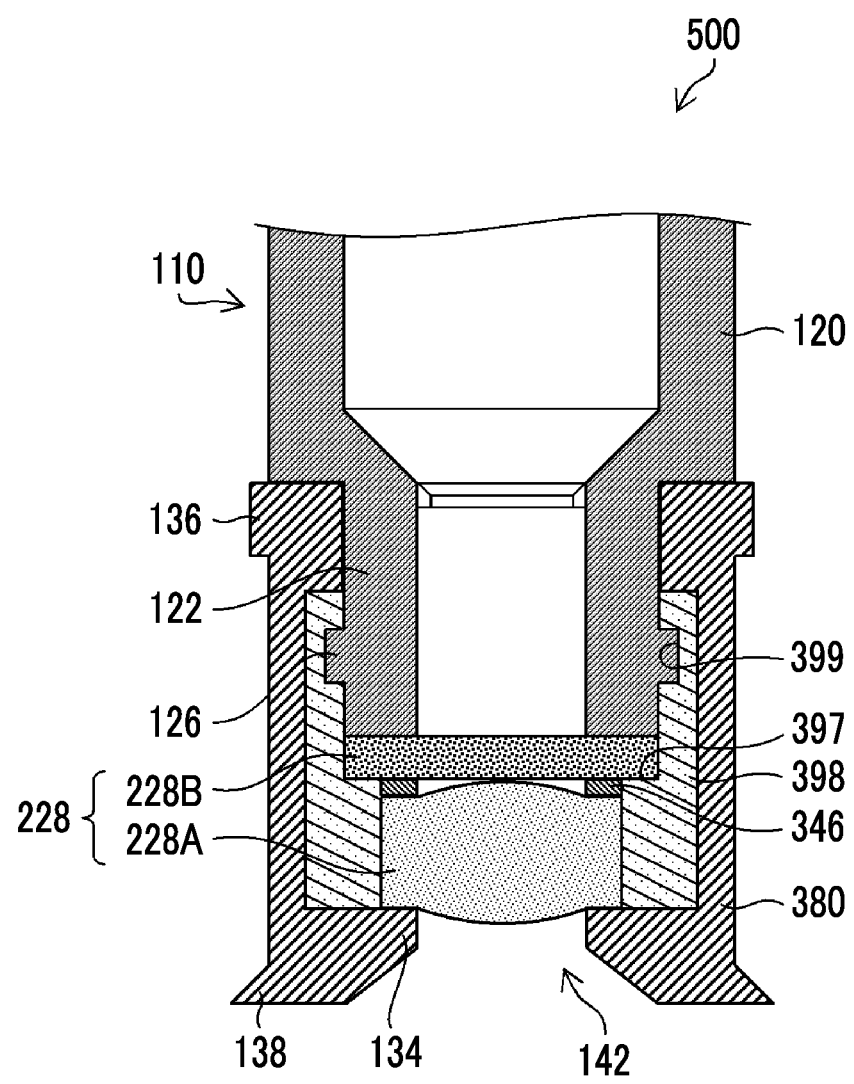
FIG. 13 is an enlarged view of still another embodiment of the tip part of the holding instrument.

FIG. 13 is an enlarged view of still another embodiment of the tip part of the holding instrument. The holding instrument 500 illustrated in FIG. 13 differs from the holding instrument 450 illustrated in FIG. 12 in that a spacer 346 is provided between the first filter 228A and the second filter 228B. As illustrated in FIG. 13, since the spacer 346 is provided, first, the second filter 228B is pressed and held by the reduced diameter part 122 of the cylinder 110 and the stepped part 397 of the holder 398 in the same manner as in FIG. 12. In addition, the first filter 228A is pressed by the reduced diameter part 122 and the first protrusion part 134 and is held through the second filter 228B and the spacer 346. Further, the second filter 228B is held by the reduced diameter part 122 and the stepped part 397, and, in addition, is pressed by the reduced diameter part 122 and the first protrusion part 134 to be held through the first filter 228A and the spacer 346. Since the spacer 346 is provided between the first filter 228A and the second filter 228B, the first filter 228A can be pressed by the first protrusion part 134 and the spacer 346. Further, the second filter 228B can be pressed by the reduced diameter part 122 and the spacer 346. As a result, the first filter 228A and the second filter 228B can be reliably held.

Figure 14:
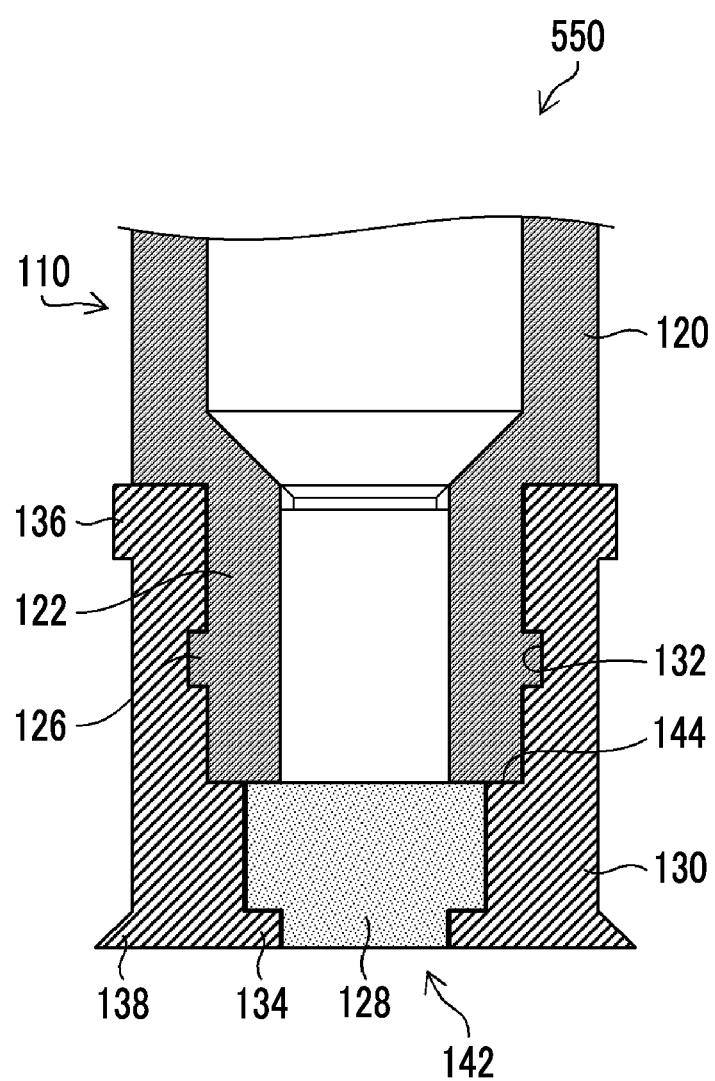
FIG. 14 is an enlarged view of still another embodiment of the tip part of the holding instrument.

FIG. 14 to FIG. 17 are enlarged views of still another embodiment of the tip part of the holding instrument. In the embodiments illustrated in FIG. 6 to FIG. 13, the filter is held by being pressed by the sealing member and the reduced diameter part of the cylinder; however, the aspect of holding the filter is not limited to this. In a holding instrument 550 illustrated in FIG. 14, the filter 128 is held by being pressed in the lateral direction (in the side direction) by the L-shaped first protrusion part 134 of the sealing member 130. In addition to providing an L-shaped protrusion part as illustrated in FIG. 14, in a case of being compressed in the lateral direction, the filter 128 can be held by being compressed in the lateral direction, by being inclined to narrow the tip side so that the first protrusion part 134 expands toward the tip side of the first protrusion part 134 as in a holding instrument 600 illustrated in FIG. 15.

Figure 16:
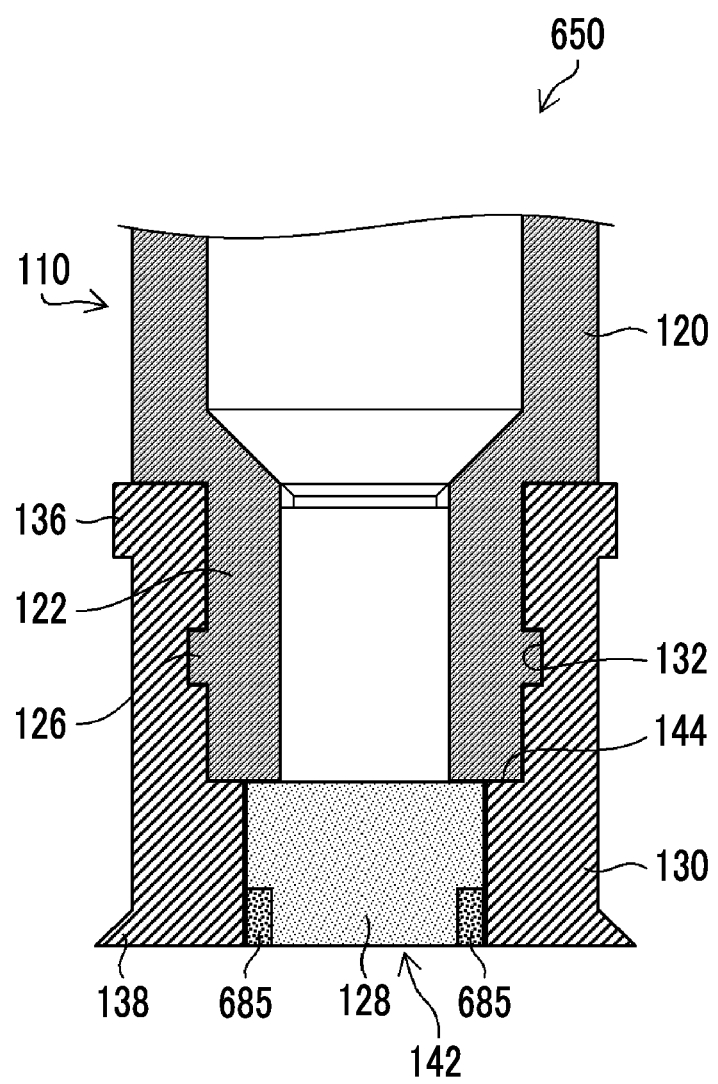
FIG. 16 is an enlarged view of still another embodiment of the tip part of the holding instrument.
Figure 17:
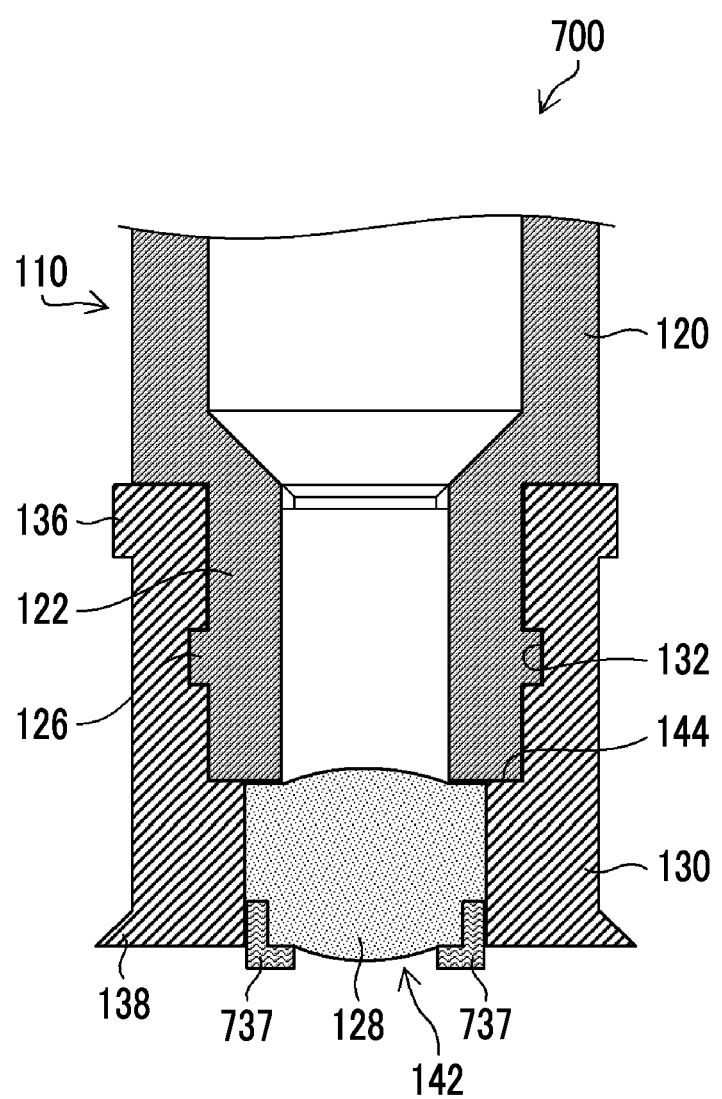
FIG. 17 is an enlarged view of still another embodiment of the tip part of the holding instrument.

Further, as in a holding instrument 650 illustrated in FIG. 16, the sealing member 130 and the filter 128 may be fixed by an adhesive 685. As a material that is used as the adhesive 685, it is preferable to use a material that does not hydrophobize the filter. Further, in a holding instrument 700 illustrated in FIG. 17, a holding member 737 is provided in the sealing member 130, and thus the filter 128 is held by being pressed in the vertical direction by the holding member 737 and the reduced diameter part 122.

Figure 15:
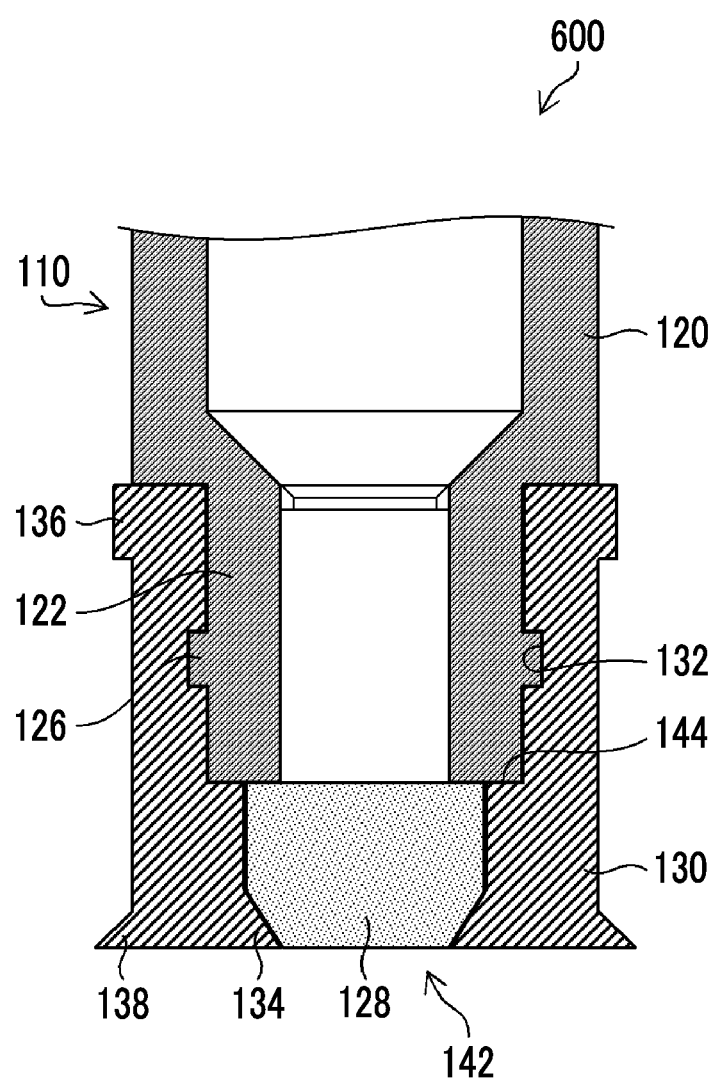
FIG. 15 is an enlarged view of still another embodiment of the tip part of the holding instrument.

In the holding instruments illustrated in FIG. 14 to FIG. 16, since the filter is pressed in the lateral direction or the filter is held by an adhesive, the end part of the filter is not compressed. However, the method of holding the filter is not limited. In a case where a material that does not easily generate siloxane is used as a material for the sealing member 130, the filter can be prevented from becoming hydrophobized, and thus blood separation can be stably carried out.

As described above, according to the present embodiment, in a case where the Shore A hardness of the sealing member is set to 20 or more and 90 or less, the smoothness between the accommodation instrument and the holding instrument can be ensured, and the liquid tightness in a case where the cylinder is inserted into the blood collection container can be secured. Further, in a case where the residual siloxane concentration of the sealing member is set to 1 wt % or less, the generation of siloxane from the sealing member can be suppressed, the filter can be prevented from being hydrophobized, and thus blood separation can be effectively carried out.

EXPLANATION OF REFERENCES

1: accommodation instrument
10: blood collection container
12: screw part
14: locking part
16: bottom part
18: leg part
20: slit groove
22: diluent
24: cap
26: packing
100, 200, 250, 300, 350, 400, 450, 500, 550, 600, 650, 700: holding instrument
110: cylinder
112: cap
114: sealing member
116: expanded diameter part
118: thin-wall portion
120: body part
122: reduced diameter part
124: locking protrusion part
126: outer flange part
128, 228: filter
130, 380: sealing member
132: groove
134: first protrusion part
136: second protrusion part
138: third protrusion part
142: inflow port
144: stepped part
152: grip part
154: mandrel part
156: space
158: lower end part
160: stepped part
162: upper end part
164: apex part
228A: first filter 228B: second filter
346: spacer
397: stepped part
398: holder
399: groove
685: adhesive
737: holding member

What is claimed is:

1. A biological specimen separation instrument comprising:
   a first container for accommodating a collected biological specimen;
   a filter for filtering a predetermined component in the collected biological specimen; and
   a second container for accommodating the predetermined component filtered by the filter, the second container being configured to be inserted into the first container,
   wherein the filter is provided on a tip side of the second container in a direction of insertion into the first container,
   a sealing member is provided in an outer circumference on the tip side of the second container in the direction of insertion to allow movement in the first container, in a state of being liquid-tightly brought into contact with an interior wall of the first container,
   the sealing member has a Shore A hardness of 20 or more and 90 or less and has a residual siloxane concentration of 1 wt % or less,
   the sealing member has an inflow port which allows entry of the biological specimen into the filter, and
   the inflow port has a diameter which decreases toward the filter.

2. The biological specimen separation instrument according to claim 1,
   wherein the filter is directly held by the sealing member.

3. The biological specimen separation instrument according to claim 1,
   wherein the residual siloxane concentration is 0.01 wt % or less.

4. The biological specimen separation instrument according to claim 1,
   wherein the filter is a hydrophilic filter.

5. The biological specimen separation instrument according to claim 1,
   wherein the filter is held in the second container by an end part of the filter being pressed in a thickness direction, and
   a thickness of a central part of the filter is thicker than a thickness of the end part of the filter.

6. The biological specimen separation instrument according to claim 1,
   wherein the scaling member includes a protrusion part on an outer circumference of the inflow port.

7. The biological specimen separation instrument according to claim 1,
   wherein the sealing member is made of any one of fluororubber, isoprene rubber, butyl rubber, chlorinated butyl rubber, or a thermoplastic elastomer.

8. The biological specimen separation instrument according to claim 7,
   wherein the thermoplastic elastomer is any one of a polystyrene-based thermoplastic elastomer, a polyolefin-based thermoplastic elastomer, a vinyl chloride-based thermoplastic elastomer, a polyurethane-based thermoplastic elastomer, a polyester-based thermoplastic elastomer, a polyamide-based thermoplastic elastomer, or a polybutadiene-based thermoplastic elastomer.

9. The biological specimen separation instrument according to claim 1,
   wherein the filter includes a first filter and a second filter disposed in this order from the inflow port.

10. The biological specimen separation instrument according to claim 9,
    wherein a surface facing the first filter in the second filter, has an area larger than an area of a surface facing the second filter in the first filter.

11. The biological specimen separation instrument according to claim 9, comprising
    a spacer provided between the first filter and the second filter.

* * * * *